US 8,735,628 B2

(12) United States Patent
Hill et al.

(10) Patent No.: US 8,735,628 B2
(45) Date of Patent: May 27, 2014

(54) PROCESSES FOR FORMING ALKYLATED ARYL PHOSPHITE COMPOSITIONS FROM COMPLEX HYDROCARBON STREAMS

(75) Inventors: Jonathan S. Hill, Manchester (GB); Maurice Power, Manchester (GB); Paul Stott, Oxford, CT (US); Peter Smith, Avon, CT (US)

(73) Assignee: Addivant USA LLC, Middlebury, CT (US)

( * ) Notice: Subject to any disclaimer, the term of this patent is extended or adjusted under 35 U.S.C. 154(b) by 323 days.

(21) Appl. No.: 12/803,922

(22) Filed: Jul. 9, 2010

(65) Prior Publication Data

US 2011/0024677 A1 Feb. 3, 2011

Related U.S. Application Data

(60) Provisional application No. 61/230,658, filed on Jul. 31, 2009.

(51) Int. Cl.
*C08K 5/526* (2006.01)
*C09K 15/32* (2006.01)

(52) U.S. Cl.
USPC ........................................ 568/14; 252/400.24

(58) Field of Classification Search
USPC ........................................ 568/14; 252/400.24
See application file for complete search history.

(56) References Cited

U.S. PATENT DOCUMENTS

| 2,051,473 A | 8/1936 | Evans et al. |
| 3,056,823 A | 10/1962 | Hechenbleikner et al. |
| 3,639,490 A | 2/1972 | Brown et al. |
| 3,872,173 A | 3/1975 | Berthoux et al. |
| 4,568,778 A | 2/1986 | Imanari et al. |
| 4,914,246 A | 4/1990 | Oswald et al. |
| 2007/0021537 A1 | 1/2007 | Chafin et al. |

FOREIGN PATENT DOCUMENTS

| CA | 2464551 | 11/2005 |
| FR | 2235902 | 1/1975 |
| GB | 953929 | 4/1964 |
| GB | 1 427 876 | 3/1976 |
| JP | 59-30842 | 2/1984 |
| WO | WO 93/03092 | 2/1993 |
| WO | WO 2006/066947 A1 | 6/2006 |
| WO | WO 2007/149143 A2 | 12/2007 |

OTHER PUBLICATIONS

U.S. Appl. No. 11/787,531.
PCT Search Report—International Application No. PCT/US2010/041772.

*Primary Examiner* — Johann R Richter
*Assistant Examiner* — Mark Luderer
(74) *Attorney, Agent, or Firm* — D'Hue Law LLC; Cedric A. D'Hue

(57) ABSTRACT

Processes for alkylating hydroxyaryl compounds by reacting a hydroxyaryl with at least one olefin of a complex hydrocarbon stream. The complex hydrocarbon stream preferably comprises a fraction of a cracked hydrocarbon feed stream or the reaction products of a dehydrogenation of a paraffinic feedstock. The olefin of the complex hydrocarbon stream is preferably a branched olefin, e.g., isobutylene or isoamylene. The alkylated compositions are suitable for forming liquid phosphite compositions.

11 Claims, 1 Drawing Sheet

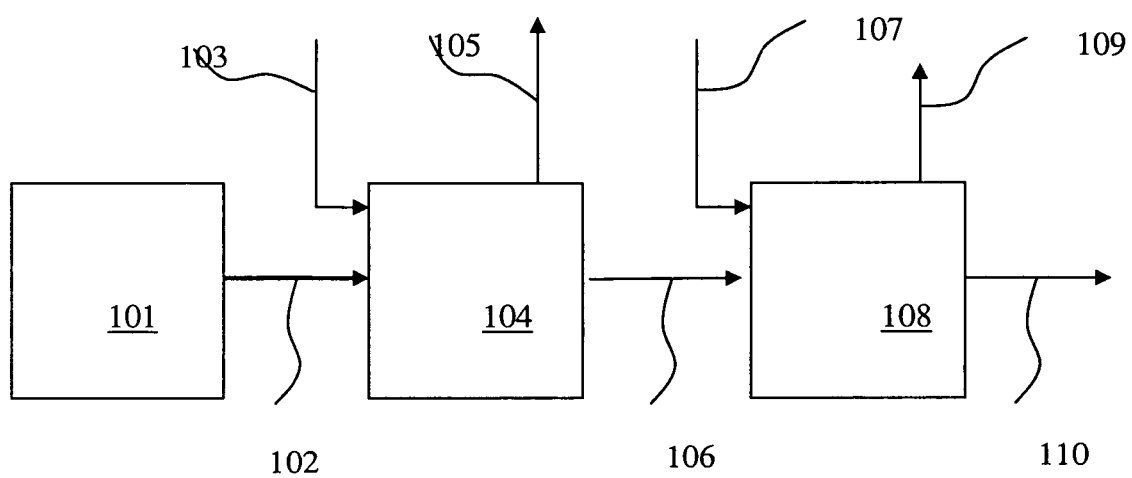

PROCESSES FOR FORMING ALKYLATED ARYL PHOSPHITE COMPOSITIONS FROM COMPLEX HYDROCARBON STREAMS

This application claims benefit under 35 USC 119(e) of U.S. provisional application No. 61/230,658, filed Jul. 31, 2009, the disclosure of which is incorporated by reference.

FIELD OF THE INVENTION

The present invention relates to producing alkylated hydroxyaryls from complex hydrocarbon streams. Additionally, it relates to the use of alkylate compositions in the production of phosphite antioxidants for polymers.

BACKGROUND OF THE INVENTION

Alkylated hydroxyaryl compounds are used in making phosphite compounds through a reaction with $PCl_3$, as described in U.S. application Ser. No. 11/787,531, entitled "LIQUID PHOSPHITE BLENDS AS STABILIZERS," the entirety of which is incorporated herein by reference. Such organic phosphites are used as secondary antioxidants for polyolefins and elastomers.

Conventionally, alkylated hydroxyaryls have been synthesized in the reaction of an olefin with a hydroxyaryl, optionally in the presence of a suitable catalyst. The alkylation of hydroxyaryls with substantially pure olefins is a widely known method. The cracking of a hydrocarbon feed stream, such as naphtha, by fluid catalytic cracking or steam cracking, and subsequent isolation processing of one fraction of the hydrocarbon feed stream allows production of the purified lower olefins, such as $C_2$-$C_5$ olefins, e.g., ethylene, propylene, butylene, and amylene. Isomers of higher olefins obtained from cracking rapidly increase in number, making similar isolation unfeasible. The process steps for separating $C_2$-$C_5$ olefins from the feed stream increases costs and reduces total production time.

$C_4$ fractions generally contain a mixture of 1,3-butadiene, isobutene, 1-butene, trans-2-butene, cis-2-butene, butane, isobutane, vinylacetylene, ethylacetylene, and 1,2-butadiene. To obtain pure olefin isomers from a $C_4$ fraction various processing steps are often required. For example, 1,3-butadiene is removed by hydrogenation, leaving a complex hydrocarbon stream comprising isobutene, n-butene, and butane as the major components. Separation of the isobutene by distillation of the complex hydrocarbon stream, however, is difficult due to the close boiling points of the components. Isobutene may be removed from the raffinate by shape-selective isolation or by chemical reaction. Such chemical reactions include hydration, addition of methanol to isobutene over an acid ion exchange resins, and oligomerization or polymerization of isobutene. The first two chemical reactions are reversible and are used when obtaining a substantially purified isobutene. The addition of methanol to isobutene over an acid ion exchange resin forms methyl-t-butyl-ether (MTBE). Health and environmental concerns exist, however, with MTBE, especially with respect to minimizing groundwater contamination. After these chemical reactions, the remaining components of the $C_4$ complex hydrocarbon stream may be separated by extraction distillation into different substantially purified olefins and saturates.

U.S. Pat. No. 4,914,246 describes a composition comprising monoalkylphenols prepared by selectively alkylating the olefin component of thermally cracked sulfur-containing petroleum distillate derived from residua. The olefin component is a linear $C_5$-$C_{12}$ olefin.

U.S. Pat. No. 4,568,778 describes a process for producing t-amylphenols by reacting isoamylene with phenols in the presence of an inorganic solid acid catalyst or an acidic ion exchange resin catalyst. The isoamylene is obtained by hydrogenation of isoprene-extracted $C_5$ fraction.

Dimerization of ethylene and disproportionation of propene are other commercially available synthesis routes to obtain olefins, especially butene. However, dimerization of ethylene primarily produces 1-butene and 2-butene as major components.

In view of the conventional processes, the need exists for an efficient source of olefins to be utilized in the production of alkylated hydroxyaryls, and in particular in the production of alkylated hydroxyaryls that may be used, for example, in the manufacture of alkylaryl phosphites, which may be used as secondary antioxidants for polyolefins and elastomers.

SUMMARY OF THE INVENTION

In a first aspect, the invention is directed to a process for forming a phosphite composition comprising reacting a hydroxyaryl compound with an olefin in a complex hydrocarbon stream to form an alkylate composition comprising two or more alkylated hydroxyaryl compounds, and reacting the two or more alkylated hydroxyaryl compounds with a phosphorous trihalide to form the phosphite composition. In one embodiment, the complex hydrocarbon stream comprises from 45 to 95 wt. % of a branched olefin and from 0.5 to 20 wt. % of a saturate. The complex hydrocarbon stream may also comprise other isomers such as linear olefins. The resultant phosphite composition comprises at least two different phosphites and is a liquid at ambient conditions. The at least two different phosphites comprise the following: tris(dialkylaryl)phosphite, tris(monoalkylaryl)phosphite, bis(dialkylaryl)monoalkylaryl phosphite, and bis(monoalkylaryl) dialkylaryl phosphite.

In a second aspect, the invention is related to a process for forming a phosphite composition comprising at least two phosphites, the process comprising the steps of: (a) providing a complex hydrocarbon stream comprising at least one olefin and at least one saturate compound; (b) contacting a hydroxyaryl with the complex hydrocarbon stream under conditions effective to form two or more alkylated hydroxyaryls in a reaction mixture; (c) separating the at least one saturate compound from the reaction mixture; and (d) reacting the two or more alkylated hydroxyaryls with a phosphorous trihalide to form the phosphite composition. Preferably, the resultant phosphite composition is liquid at ambient conditions.

In a third aspect, the present invention is related to an integrated reaction system for forming a phosphite composition, comprising: (a) a petrochemical refining system for forming a complex hydrocarbon stream comprising at least one olefin; (b) an alkylate synthesis reactor in fluid communication with the petrochemical refining system and in which the olefin from the complex hydrocarbon stream is reacted with one or more hydroxyaryls under conditions effective to form an alkylate composition; and (c) a phosphite synthesis reactor in fluid communication with the alkylate synthesis reactor and in which the alkylate composition is reacted with a phosphorus trihalide, with or without catalyst, under conditions effective to form the liquid phosphite composition.

BRIEF DESCRIPTION OF THE DRAWING

The present invention will be better understood in view of the appended non-limiting Figure in which:

FIG. 1 illustrates an integrated reaction system for forming phosphite compositions according to one embodiment of the invention.

DETAILED DESCRIPTION OF THE INVENTION

Introduction

The present invention relates to processes for alkylating hydroxyaryl compounds, e.g., phenols or cresols, with olefins contained in a complex hydrocarbon stream. At least one olefin, preferably at least one branched olefin, from the complex hydrocarbon stream is reacted with the hydroxyaryl under conditions effective to form an alkylate composition. Preferably, the olefin is not isolated from the complex hydrocarbon stream, but is instead reacted with the hydroxyaryl in the presence of saturated components that are also contained in the complex hydrocarbon stream. These saturated components, optionally, are easily liberated from the resulting alkylate composition. The alkylate composition may be subsequently reacted with a phosphorous compound, as described below, to form a liquid phosphite composition, also described below. The inventive process advantageously reduces the process steps and commensurate costs associated with separating the olefins from the complex hydrocarbon stream.

In one embodiment the complex hydrocarbon stream is obtained from a petroleum source, such as crude oil and/or natural gas. In other embodiments, the invention relates to an integrated reaction system comprising a petrochemical refining system, an alkylation system and preferably a phosphite synthesis system. FIG. 1 illustrates an integrated reaction system 100 according to one embodiment of the invention. As shown in FIG. 1, a complex hydrocarbon stream 102 is provided by petroleum source 101. In one embodiment, the complex hydrocarbon stream 102 comprises a plurality of components including at least one saturated compound and at least one olefin (e.g., butylenes or amylenes) having the same number of carbon atoms. In integrated reaction system 100, the petroleum source 101 may comprise a petrochemical refining system, while in other embodiments the petroleum source 101 comprises an alkylate storage tank. In one embodiment, complex hydrocarbon stream 102 and hydroxyaryl stream 103 are directed to alkylation reactor 104, where they are reacted, optionally in the presence of catalyst, under conditions effective to alkylate the hydroxyaryls. Preferably, the reaction forms alkylate composition 106, which comprises two or more alkylated hydroxyaryls. As discussed above, saturates from complex hydrocarbon stream 102, preferably, are liberated from alkylation reactor 104 via vent stream 105 during the alkylation process.

In one embodiment, alkylate composition 106 and a phosphorous halide, e.g., $PCl_3$, are directed to phosphite synthesis reactor 108, where alkylate composition 106 contacts the $PCl_3$, optionally in the presence of catalyst, under conditions effective to form phosphite composition 110. Preferably, phosphite composition 110 comprises two or more alkylaryl phosphites (described below). In one embodiment, HCl is formed as a byproduct of the reaction and is liberated from the reaction mixture in HCl stream 109.

In another embodiment (not shown), the complex hydrocarbon stream may be the reaction product of a dehydrogenation of paraffinic feedstock. Dehydrogenation is a widely known method of obtaining olefins from a paraffinic feedstock. In such embodiments, the reaction products comprise at least one olefin and at least one saturate, e.g. a complex hydrocarbon stream. The conditions for dehydrogenation, preferably, should be such that the reaction product includes an olefin. Exemplary dehydrogenation conditions are set forth below. A paraffinic feedstock generally includes a $C_2$-$C_{18}$ alkane, e.g., a $C_3$-$C_8$ alkane, or a $C_4$-$C_6$ alkane. Dehydrogenation may occur at a temperature of from 250 to 800° C., e.g., 400 to 700° C., or 555 to 700° C., and under a low pressure of less than 15.0 KPa, e.g. less than 5.0 KPa, or less than 1.0 KPa. In one embodiment, the dehydrogenation temperature influences the conversion of paraffin to olefin and temperatures outside of the defined ranges may yield less olefin. Optionally, a catalyst may be used for dehydrogenation. When a catalyst is used, the catalyst should be thermally stable so as to avoid deactivation. In one embodiment, the catalyst is selected from chrome-alumina catalysts, catalyst composites comprising alumina and chromium oxide, noble metal catalysts, e.g., nickel (Ni) catalysts, palladium (Pd) catalysts, and platinum (Pt) catalysts, and transition catalysts. e.g., iron (Fe) catalysts, vanadium (V) catalysts, chromium (Cr) catalysts, and manganese (Mn) catalysts. Of course, this listing is not exhaustive. In one embodiment, the catalyst is employed in the absence of water or steam.

In other embodiments, the complex hydrocarbon stream comprises an impure olefin.

Complex Hydrocarbon Stream

As used herein, the term "complex hydrocarbon stream" refers to a mixture of hydrocarbons comprising at least one branched olefin and one of a linear olefin and a saturate. In one embodiment, a majority of the hydrocarbons, e.g., at least 80 wt. %, at least 90 wt. %, at least 92 wt. %, or at least 95 wt. %, have the same number of carbon atoms. The number of carbons atoms may vary from 2 to 18 carbon atoms, e.g., from 3 to 8 carbon atoms, or from 4 to 6 carbon atoms. In one embodiment, the hydrocarbons of the complex hydrocarbon stream have at least 2 carbon atoms, e.g., 3 carbon atoms, 4 carbon atoms, 5 carbon atoms, or up to 18 carbon atoms. Preferably, the complex hydrocarbon stream is a mixture of $C_4$ hydrocarbons and/or $C_5$ hydrocarbons.

The complex hydrocarbon stream may further comprise a minor amount of components having a higher or lower number of carbon atoms than the majority of the hydrocarbons. The minor amount may be up to 10 wt. %, e.g., up to 8 wt. %, or up to 5 wt. %, of the total amount of hydrocarbons.

In a preferred embodiment, for a complex hydrogen stream derived from petroleum sources, the type of cracking used to obtain the fraction, as well as the severity of the cracking conditions and feed stream, determines the relative amounts of each component. Cracking processes that produce branched olefins are preferred. For example, steam cracking of naptha under low severity conditions produces a $C_4$ fraction having more isobutene than fluid catalytic cracking of the same feed stream. Likewise, the dehydrogenation conditions may also influence the relative amounts of each component.

In one embodiment, the relative amounts in weight percent (wt. %) of components in the complex hydrocarbon stream is set forth in Table 1.

TABLE 1

| Component | Range | Preferred Range | Most Preferred Range |
|---|---|---|---|
| Branched Olefins | 45 to 95 wt. % | 50 to 85 wt. % | 55 to 70 wt. % |
| Straight Olefins | 1 to 50 wt. % | 5 to 43 wt. % | 10 to 43 wt. % |
| Saturates | 0.5 to 35 wt. % | 1 to 15 wt. % | 2 to 10 wt. % |

Preferably, the complex hydrocarbon stream is substantially free of dienes. In one embodiment, the complex hydrocarbon stream contains less than 500 wppm of dienes, e.g. less than 100 wppm, or no detectable amount of dienes. In one embodiment, the complex hydrocarbon stream may be a fraction obtained from the cracking process or it may be a processed fraction, e.g., a fraction that is initially separated after cracking. As an example, a processed fraction may be initially separated by removing 1,3-butadiene, thus providing a $C_4$ complex hydrocarbon stream.

It is contemplated that each of the components of the complex hydrocarbon stream may contain one or more isomers. In one embodiment, the complex hydrocarbon stream comprises at least 2 different isomers, e.g., at least 3 different isomers, or at least 5 different isomers. For example, when a $C_4$ hydrocarbon complex stream is used, the branched olefin component may comprise isobutylene. As another example, when a $C_5$ hydrocarbon complex stream is used, the branched olefin component may comprise at least 2 different isomers, namely, 2-methylbutene-2, or 2-methylbutene-1, generically referred to as isoamylene.

In an exemplary embodiment, the complex hydrocarbon stream has a $C_5$ major component and a $C_4$ minor component, as shown in Table 2.

TABLE 2

| Component | Isomers | | Wt. % |
|---|---|---|---|
| Branched Olefin | 3-methylbutene-1 | | 3.07-3.09 |
| | 2-methylbutene-2 | | 53.39-53.71 |
| | 2-methylbutene-1 | | 28.09-29.08 |
| | Isoprene | | 1.03-1.15 |
| | | Total | 85.58-87.03 |
| Linear Olefin | pentene-1 | | 0.94-0.99 |
| | trans-pentene-2 | | 1.78-2.50 |
| | cis-pentene-2 | | 1.24-1.46 |
| | n-pentenes | | 4.95-5.46 |
| | | Total | 8.91-10.41 |
| Saturates | Pentanes | | 6.69-6.89 |
| Minor Components | Isobutylene | | 0.84-1.49 |
| | Butenes | | 0.41-0.58 |
| | | Total | 1.25-2.07 |

Alkylation Process

In one embodiment, the hydroxylaryl is reacted with at least one olefin, e.g., at least two olefins, or at least three olefins, from a complex hydrocarbon stream. Preferably, the hydroxyaryl is an aromatic moiety having at least one hydroxyl and from 6 to 18 carbon atoms, e.g., phenol, 1-naphthol, 2-naphthol, 9-phenanthrol, indanol, catechol, resorcinol, anthracen-2-ol, 4-biphenol, 4,4'-biphenol, xylenol, cresol (e.g., o-, m-, and/or p-cresol), and derivatives thereof, preferably phenol. In preferred embodiments, the at least one olefin comprises a branched olefin, e.g., isobutylene or isoamylene. In still further embodiments, the hydroxyaryl is reacted with at least two olefins in the complex hydrocarbon stream, provided that one of the components is a branched olefin. The weight ratio of olefin(s) in the complex hydrocarbon stream to hydroxylaryl(s) preferably ranges from 1:1 to 6:1, e.g., from 1.1:1 to 2:1, or from 1.25:1 to 1.4:1.

In one embodiment, the other components, e.g., not branched olefins, including linear olefins or saturates do not react with the hydroxyaryl. Depending on the conditions, linear olefins may react to a greater extent than saturates. This reaction, however, is, typically, not favored. Generally, the linear olefins and/or saturates pass through the alkylation reaction.

Although conditions for the alkylation process may vary widely, in some preferred embodiments, the reaction of the phenol and the olefin may occur in an inert atmosphere (e.g., under nitrogen) at a temperature of from 60 to 160° C., e.g., from 70 to 145° C. or from 80 to 140° C. The reaction is preferably performed at a pressure of from 0.2 to 10 atm, e.g., from 0.2 to 5 atm or from 0.2 to 4 atm. In a batch reaction, the reaction time may last from 1 to 12 hours, e.g., from 2 to 10 hours, or from 3 to 5 hours. In a continuous reaction, the residence time may be from 0.1 to 5 hours, e.g., from 0.2 to 4 hours or from 0.5 to 1 hour. The alkylation preferably is performed in the presence of a catalyst. The catalyst may, for example, be selected from the group consisting of acid clay catalyst, cationic ion exchange resins, Brönsted acids, e.g., sulfuric acid, trifluoromethanesulfonic acid (triflic acid) and phosphotungstic acid, or Lewis acids, e.g., $BF_3$. Suitable commercial acid clay catalysts include Fulcat™ 22B (Rockwood Additives). In one embodiment, the sulfonic acid-type cation-exchange resin catalyst useful in the present invention can be, for example, a sulfonated styrene-divinyl benzene copolymer, a sulfonated crosslinked styrene polymer, a phenol formaldehyde-sulfonic acid resin, or a benzene formaldehyde-sulfonic acid resin. Cation exchange resins useful in the present invention include for example styrene-divinylbenzene types of strong acid ion exchange resins such as Dowex™ 50WX4, Dowex 50WX2, Dowex M-31, Dowex Monosphere M-31, Dowex DR-2030 and Dowex Monosphere DR-2030 catalysts (Dow Chemical). Other appropriate resins include: Amberlyst™ 15, Amberlyst 131, Amberlyst 35, Amberlyst 36, and A21 (Rohm and Hass, subsidiary of Dow); Diaion™ WA30, Diaion SK104, Diaion SK1B, Diaion PK208, Diaion PK212 and Diaion PK216 (Mitsubishi); Tulsion™ T-38, Tulsion T-62, Tulsion T-66, Tulsion T-3825 and Tulsion T-3830 (Thermax); Lewatit™ K1131, Lewatit K1221, Lewatit K1261 and Lewatit SC 104 (Sybron Chemicals); Indion™ 180 and Indion 225 (Ion Exchange (India) Limited); and Purolite™ CT-175, Purolite™ CT-169, and Purolite™ CT-275(Purolite).

In one embodiment, a mild catalyst, such as, e.g., aluminum-containing catalysts, e.g., aluminum chloride or aluminum phenolate, is utilized. In one embodiment, such catralysts may be created in situ during the alkylation reaction by dissolving aluminum in the phenol.

In one embodiment, a batch alkylate synthesis takes place in a pot-type reactor. In another embodiment, the alkylate synthesis is conducted on a continuous basis in a continuous type reactor. In the continuous process, the alkylation reaction is optionally quenched using a polar solvent, water, that forms a liquid phase containing most, if not all, of the catalyst and a organic phase containing the alkylated aryl compound, which may be removed by distillation. When the continuous process takes place over a fixed bed of solid catalyst a quenching step may not be necessary.

In one aspect of the process, any free phenolic compounds that are not reacted with the olefin may be removed from the mixture of reaction products through distillation at a temperature, for example, of from 70 to 160° C. and at a pressure of from 1 to 10 mbar.

According to embodiments of the present invention, the reaction of the hydroxyaryl and the olefin from the complex hydrocarbon stream produces a mixture of reaction products. The alkylate composition may comprise, for example, from 5 to 95 wt %, e.g., from 10 to 70 wt %, or from 30 to 65 wt %, of a p-alkylated phenol, and from 5 to 95 wt %, e.g., from 10 to 70 wt %, or from 30 to 65 wt %, of an o,p-dialkylated phenol.

In one embodiment, the hydroxyaryl may be alkylated in the ortho and para positions with the component from the complex hydrocarbon stream. In other embodiment, the hydroxyaryl is dialkylated in the ortho and para positions. The para position is preferred, and the amount of hydroxyaryls substituted in the para position, either mono or disubstituted, is at least 85 wt. %, e.g., at least 90 wt. %, or at least 95 wt. %. Similarly, it is preferred that few if any of the hydroxyaryls are monosubstituted in the ortho position. Preferably, the hydroxyaryls are monosubstituted in the ortho position in an amount less than 3 wt. %, e.g., less than 2 wt. %, or less than 1.0 wt %.

Although the hydroxyaryl may be tri-substituted, it is preferred that few if any of the hydroxyaryls are trisubstituted. For example, in some embodiments fewer than 3%, e.g., fewer than 2%, or fewer than 1%, of the hydroxyaryls are trisubstituted. In one embodiment, the phosphite composition is substantially free of trisubstituted hydroxyaryls.

In one embodiment, saturates in the complex hydrocarbon stream do not react during the alkylating process and are separated, e.g., easily separated, from the product alkylate composition. Due to the high vapor pressure of the saturate compounds relative to the alkylates in the alkylate composition, it is preferred that substantially all of the saturates, e.g., at least 80 wt.%, at least 95 wt.%, or at least 99 wt.%, vaporize during the alkylation process and thus may be vented from the alkylate composition during the alkylation reaction. In still other embodiments, a minor distillation step may be desired to completely remove any residual unreacted components from the alkylate composition. In one aspect of the process, any free hydroxyaryls, e.g., free phenols, that are not reacted with the olefin from the complex hydrocarbon stream may be removed as described above.

Advantageously, by reacting olefins in a complex hydrocarbon stream with a hydroxyaryl to form the alkylate composition, production costs associated with employing purified olefins can be reduced or eliminated. In some applications, the alkylate synthesis processing equipment may be integrated with a petrochemical refining facility to further reduce processing times and transportation and storage costs. Such integrated reaction systems also eliminate or reduce storage and transportation costs associated with employing purified olefins. Preferably, the integrated reaction system comprises a petrochemical refining system that forms the complex hydrocarbon stream from one or more fractions and an alkylate synthesis reactor as described herein. In further embodiments, the phosphite synthesis reactors, as described herein, are integrated with the petrochemical refining facility and the alkylating system.

In addition, alkylating in the presence of saturated hydrocarbons increases selectivity. One problem with conventional alkylation systems, and in particular $C_4$ alkylation systems, is that butylene undesirably tends to dimerize at elevated temperatures and pressures and forms various $C_8$ compounds, which may alkylate the hydroxyaryl leading to undesirably "heavy" byproducts, as shown in the following reaction scheme. Similar reactions would be expected with $C_5$ olefins.

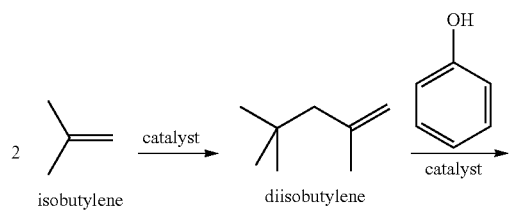

isobutylene    diisobutylene

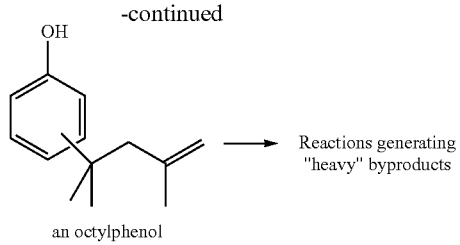

an octylphenol

Reactions generating "heavy" byproducts

One advantage of alkylating hydroxyaryls in the presence of saturated components, in particular for $C_4$ alkylation systems, is that olefin dimerization is effectively reduced, resulting in increased selectivity to the desired alkylate products. This is demonstrated in Example 1, below. In some preferred embodiments, for example, hydroxyaryls that are alkylated with dimer and other "heavy" alkyl groups may be less than 1.0 mole %, e.g., less than 0.5 mole %, or less than 0.4 mole %.

Synthesis of Liquid Phosphite Compositions

The present invention also relates to methods for making liquid phosphite compositions from the alkylated compositions obtained by using the complex hydrocarbon stream. In one embodiment, the alkylate composition, optionally formed from the above-described alkylate composition synthesis process, is further reacted with a phosphorus trihalide, with or without catalyst, to form a liquid phosphite composition. The phosphorus trihalide preferably is selected from phosphorus trichloride and phosphorus tribromide. When a catalyst is used, the catalyst may be selected from the group consisting of pyridine, N,N-dimethyldodecylamine, dilauryl methyl amine, trialkylamine, and the hydrochloride salts thereof. The molar ratio of alkylate composition (i.e., alkylated phenol compounds) to phosphorus trihalide preferably is from 3:1 to 5:1, e.g., from 3:1 to 4:1 or from 3.1 to 3.7:1.

The reaction of the alkylated phenols with a phosphorus trihalide may be conducted under an inert atmosphere (e.g., nitrogen) at a temperature of from 5 to 70° C., e.g., from 40 to 70° C. or from 50 to 70° C. The phosphorus trihalide may be charged to the reactor and the alkylate composition may be added thereto. In this case, preferably, the temperature is held at or below 70° C. during the addition of the phosphorus trihalide to the alkylate composition to prevent refluxing the phosphorus trihalide. After the addition of phosphorus trihalide, the temperature is optionally held for 10 minutes to 12 hours, e.g., from 30 minutes to 10 hours, or from 1 hour to 3 hours. The reaction preferably is conducted at a pressure of 0.8 to 4 atm, e.g., from 0.9 to 3 atm or from 1 to 2 atm. Optionally, the alkylate composition may be charged to the reactor and the phosphorus trihalide added thereto. Next, the temperature may be ramped to a ramped temperature ranging from 70° C. to 250° C., e.g., from 80° C. to 225° C. or from 90° C. to 200° C. Preferably, the reaction is held at the ramped temperature for from 10 minutes to 12 hours, e.g., from 30 minutes to 10 hours, or from 1 hour to 3 hours. The reaction preferably is conducted at a reduced pressure of 0.01 to 0.5 atm, e.g. from 0.03 to 0.4 atm or from 0.04 to 0.1 atm. During the reaction time, hydrochloric or hydrobromic gas will be evolved, and may be removed by reducing the pressure to about 0.05 atm or sweeping an inert gas such as nitrogen over the reaction mixture. In one aspect the removal of such gases may be performed until the total chloride content in the reaction mixture is less than 50 wppm, e.g., less than 25 wppm or less than 10 wppm.

In one aspect of the process, any free hydroxyaryls, e.g., cresols or phenols, that are not reacted with the phosphorus trihalide may be liberated by raising the reaction temperature to up to 275° C., e.g., up to 250° C. or up to 225° C., and in a vacuum at a pressure of 0.0001 to 0.1 atm. In one embodiment, a wiped-film molecular (Short-Path) stills, wiped film evaporators (WFE), thin film evaporators, or similar equipment may be used to further remove the free hydroxyaryls.

In one embodiment, the step of forming the phosphite composition may occur in one or more neutral solvents. Typical solvents that may be employed include toluene, xylene, methylene chloride, heptane, chloroform, and benzene.

In one embodiment, the liquid phosphite compositions of the present invention are obtained in a direct chemical reaction, in which the molar ratio of the alkylated phenol is adjusted to yield a phosphite composition that is a liquid at ambient conditions. A schematic of one reaction method that may be employed to form such phosphite compositions is as follows.

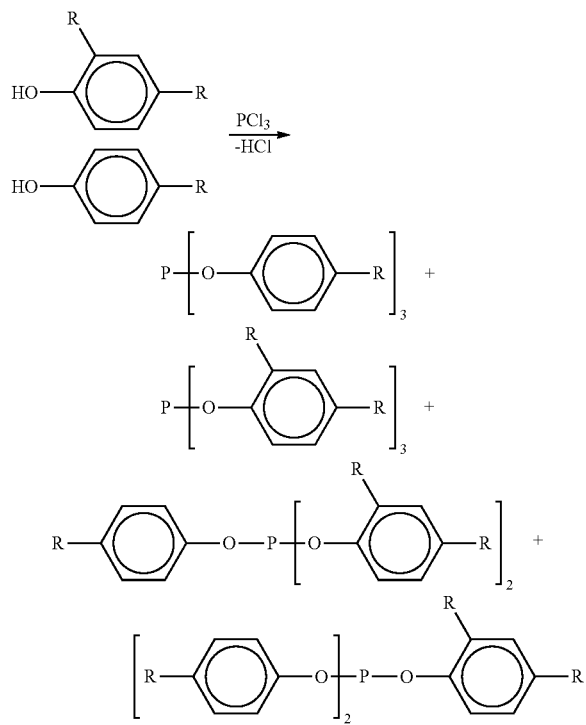

wherein each R is independently $R_4$, $R_5$, and $R_6$ as defined below. Note that a minor amount of other alkylated phenols, e.g., ortho-substituted monoalkylated phenol, may be included as an additional reactant in the above reaction scheme and would form additional derivative phosphites, but these additional reactants and products have been omitted from this reaction for clarity.

Phosphites

In one embodiment, the present invention generally relates to a composition, produced by the embodied methods, comprising at least two different phosphites of the structure:

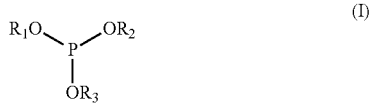 (I)

wherein $R_1$, $R_2$, and $R_3$ are independently selected alkylated aryl groups and wherein said composition is a liquid at ambient conditions. By "ambient conditions" it is meant room temperature, e.g., 25° C., and 1 atmosphere pressure.

The aryl moiety present in the compounds of the present invention is preferably an aromatic moiety of from 6 to 18 carbon atoms, e.g., phenyl, naphthyl, phenanthryl, anthracyl, biphenyl, terphenyl, o-cresyl, m-cresyl, p-cresyl, and the like, preferably phenyl. Each aromatic moiety is substituted with at least one $C_1$-$C_{18}$, e.g., $C_4$-$C_{10}$, or $C_4$-$C_5$ alkyl group, but preferably no aromatic moieties are substituted with any $C_9$ alkyl groups. The alkyl substituent(s) on the aryl moieties are selected from straight-chain or branched $C_1$-$C_{18}$ alkyl, e.g., $C_1$-$C_8$ alkyl, $C_4$-$C_6$ alkyl, $C_4$-$C_5$ alkyl, $C_4$ alkyl, or $C_5$ alkyl. Preferably, the alkyl substituent(s) is not $C_s$-$C_{10}$ alkyl, e.g., not $C_9$ alkyl. The alkyl substituent may include, for example, methyl, ethyl, propyl, butyl, amyl, hexyl, heptyl, octyl, nonyl (although less preferred), decyl, undecyl, dodecyl, tridecyl, tetradecyl, pentadecyl, hexadecyl, heptadecyl, octadecyl, and isomers thereof. Most preferably, the alkyl group(s) are selected from butyl, especially sec-butyl, t-butyl, and amyl groups, especially sec-amyl, t-amyl and neo-amyl. As indicated, in a preferred embodiment, the alkyl moieties do not include nonyl, Meaning the phosphite composition preferably comprises less than 50 wppm, e.g., less than 10 wppm or less than 5 wppm nonyl substituted aryl phosphite compounds, and most preferably no detectable nonyl substituted aryl phosphite compounds. In addition, the phosphite composition preferably comprises less than 50 wppm, e.g., less than 10 wppm or less than 5 wppm nonylphenol, and most preferably no detectable nonylphenol. Most preferably, the alkyl group(s) are independently selected from propyl, butyl, especially, isopropyl, sec-butyl, t-butyl, amyl, especially sec-amyl, t-amyl neo-amyl, and dodecyl.

In a preferred embodiment, the phosphite composition comprises at least two different phosphites, e.g., at least three different phosphites, or at least four different phosphites, selected from the group consisting of a tris(dialkylaryl)phosphite, a tris(monoalkylaryl)phosphite, a bis(dialkylaryl) monoalkylaryl phosphite, and a bis(monoalkylaryl)dialkylaryl phosphite. Thus, the phosphite composition comprises at least one phosphite that has at least one aromatic moiety that is multiply substituted, such as a bis(dialkylaryl) monoalkylaryl phosphite, a bis(monoalkylaryl)dialkylaryl phosphite or a tris(dialkylaryl) phosphite. In one aspect, the phosphite composition includes at least one phosphite compound in which each aryl moiety is monosubstituted, e.g., a tris(monoalkylaryl) phosphite.

In one embodiment, the phosphite composition is substantially free of phosphite compounds having aryl groups that are substituted with alkyl groups having hydrogen atoms in the a position. That is, in preferred embodiments, at least 95%, at least 98%, or at least 99% of the aryl moieties are substituted with alkyl groups having tertiary α-carbons, most preferably t-butyl and/or t-amyl. T-butyl may be derived from isobutylene in a complex hydrocarbon stream of a $C_4$ fraction, and t-amyl may be derived from isoamylene in a complex hydrocarbon stream of a $C_5$ fraction.

In one embodiment, $R_1$, $R_2$, and $R_3$ are independently selected alkylated aryl groups of the structure:

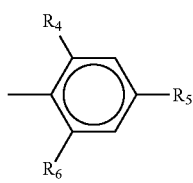

(II)

wherein $R_4$, $R_5$, and $R_6$ are independently selected from the group consisting of hydrogen and $C_1$-$C_8$ alkyl, e.g., methyl, ethyl, propyl, butyl, amyl, hexyl, heptyl, octyl, and isomers thereof, e.g., isopropyl, t-butyl, t-amyl, neo-amyl, provided that at least one of $R_4$, $R_5$, and $R_6$ is not hydrogen, e.g., at least one of $R_4$, $R_5$, and $R_6$ is $C_1$-$C_8$ alkyl. In one embodiment $R_4$ and $R_6$ are hydrogen, and $R_5$ is not hydrogen, e.g., $R_5$ is $C_1$-$C_8$ alkyl. In one embodiment, $R_4$ and $R_5$ are not hydrogen, e.g., $R_4$ and $R_5$ are independently selected $C_1$-$C_8$ alkyl, and $R_6$ is hydrogen. In one embodiment, either or both ortho alkyl groups, e.g., $R_4$ and $R_6$, have no α-hydrogen atoms, e.g., either or both ortho alkyl groups, e.g., $R_4$ and $R_6$, have tertiary α-carbon atoms selected from the group consisting of t-butyl and t-amyl.

In one embodiment, $R_4$ and $R_5$ are independently selected from the group consisting of methyl, ethyl, propyl, butyl, amyl, hexyl, and isomers thereof, and $R_6$ is hydrogen. In another embodiment, $R_4$ and $R_6$ are hydrogen and $R_5$ are independently selected from the group consisting of methyl, ethyl, propyl, butyl, amyl, hexyl, and isomers thereof. In one aspect of these embodiments, at least one of $R_4$, $R_5$, and $R_6$ are $C_4$ or $C_5$ alkyl, most preferably t-butyl or t-amyl.

In various optional embodiments, the alkylated aryl groups for $R_1$, $R_2$, and $R_3$ are provided as shown in Table 3. The phosphite compositions of the invention may comprise any two or more of these compounds in amounts sufficient that the phosphite composition is a liquid at ambient conditions.

In one embodiment, $R_1$, $R_2$, and $R_3$ are independently selected alkylated aryl groups of the structure:

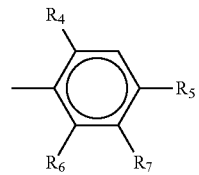

(III)

wherein $R_4$, $R_5$, and $R_6$ are defined above and $R_7$ is hydrogen or methyl, provided that one of $R_4$, $R_5$, $R_6$, and $R_7$ is methyl and that at least two of $R_4$, $R_5$, $R_6$, and $R_7$ are not hydrogen. Such phosphites may be formed, for example, by the reaction of one or more alkylated cresol compounds, e.g., one or more of alkylated ortho-, meta-, and/or para-cresol, with $PCl_3$, as discussed in greater detail herein.

In some preferred embodiments of the present invention, the phosphite composition comprises at least two phosphites selected from the group consisting of tris(4-t-butylphenyl) phosphite, tris(2-t-butylphenyl)phosphite, tris(2,4-di-t-butylphenyl)phosphite, bis(4-tbutylphenyl)-2,4-di-t-butylphenyl phosphite, bis(2,4-di-t-butylphenyl)-4-t-butylphenyl phosphite, bis(2-tbutylphenyl)-2,4-di-t-butylphenyl phosphite, bis(2,4-di-t-butylphenyl)-2-t-butylphenyl phosphite, tris(4-t-amylphenyl)phosphite, tris(2-t-amylphenyl)phosphite, tris(2,4-di-t-amylphenyl)phosphite, bis(4-t-amylphenyl)-2,4-di-t-amylphenyl phosphite, bis(2,4-di-t-amylphenyl)-4-t-amylphenyl phosphite, bis(2-t-amylphenyl)-2,4-di-t-amylphenyl phosphite, and bis(2,4-di-t-amylphenyl)-2-t-amylphenyl phosphite.

In some embodiments, the phosphite compositions have an overall phosphorus content that is equal to or greater than TNPP, e.g., at least 4.5 mole %, e.g., at least 4.8 mole %, or at least 5.1 mole %. In terms of ranges, the overall phosphorus content of the phosphite composition may range, for

TABLE 3

| | $R_1$ | | | $R_2$ | | | $R_3$ | | |
|---|---|---|---|---|---|---|---|---|---|
| # | $R_4$ | $R_5$ | $R_6$ | $R_4$ | $R_5$ | $R_6$ | $R_4$ | $R_5$ | $R_6$ |
| 1 | H | t-butyl | H | H | t-butyl | H | H | t-butyl | H |
| 2 | t-butyl | t-butyl | H | H | t-butyl | H | H | t-butyl | H |
| 3 | t-butyl | t-butyl | H | t-butyl | t-butyl | H | H | t-butyl | H |
| 4 | t-butyl | t-butyl | H | t-butyl | t-butyl | H | t-butyl | t-butyl | H |
| 5 | H | t-amyl | H | H | t-amyl | H | H | t-amyl | H |
| 6 | t-amyl | t-amyl | H | H | t-amyl | H | H | t-amyl | H |
| 7 | t-amyl | t-amyl | H | t-amyl | t-amyl | H | H | t-amyl | H |
| 8 | t-amyl | t-amyl | H | t-amyl | t-amyl | H | t-amyl | t-amyl | H |
| 9 | H | t-butyl | H | H | t-butyl | H | H | t-amyl | H |
| 10 | H | t-butyl | H | H | t-amyl | H | H | t-amyl | H |
| 11 | t-butyl | t-butyl | H | H | t-butyl | H | H | t-amyl | H |
| 12 | t-butyl | t-butyl | H | H | t-amyl | H | H | t-amyl | H |
| 13 | t-butyl | t-amyl | H | H | t-amyl | H | H | t-amyl | H |
| 14 | t-amyl | t-amyl | H | H | t-butyl | H | H | t-amyl | H |
| 15 | t-amyl | t-amyl | H | H | t-butyl | H | H | t-butyl | H |
| 16 | t-butyl | t-butyl | H | t-butyl | t-butyl | H | H | t-amyl | H |
| 17 | t-butyl | t-butyl | H | t-butyl | t-butyl | H | H | t-butyl | H |
| 18 | t-butyl | t-amyl | H | t-butyl | t-amyl | H | H | t-butyl | H |
| 19 | t-amyl | t-amyl | H | t-amyl | t-amyl | H | H | t-butyl | H |
| 20 | t-butyl | t-amyl | H | t-butyl | t-butyl | H | t-butyl | t-butyl | H |
| 21 | t-butyl | t-amyl | H | t-butyl | t-amyl | H | t-amyl | t-butyl | H | example, from 4.5 to 10.0 mole %, e.g., from 4.8 to 8.0 mole %, or from 5.1 to 6.0 mole %, based on the total moles of all phosphorous-containing compounds in the phosphite composition.

As indicated above, in a preferred embodiment, the phosphite composition comprises at least two of the following: a tris(dialkylaryl)phosphite, a tris(monoalkylaryl)phosphite, a bis(dialkylaryl)monoalkylaryl phosphite, and a bis(monoalkylaryl)dialkylaryl phosphite, wherein the phosphite composition is a liquid at ambient conditions. The relative amounts of the respective phosphite components contained in these phosphite compositions may vary somewhat so long as the phosphite composition itself is a liquid at ambient conditions. In terms of ranges, for example, the phosphite composition preferably comprises tris(monoalkylaryl)phosphites, e.g., tris(4-t-amylphenyl)phosphite, in an amount from 20 to 70 wt. %, e.g., from 15 to 55 wt. %, or from 37 to 54 wt. % and bis(monoalkylaryl)diamylaryl phosphites, e.g., bis(4-t-amylphenyl)-2,4-di-t-amylphenyl)phosphite, in an amount from 15 to 60 wt. %, e.g., from 31 to 50 wt. %, or from 34 to 45 wt. %. Optionally, the phosphite composition further comprises tris(dialkylaryl)phosphites and/or bis(dialkylaryl)monoalkylaryl phosphites. If present, the tris(dialkylaryl)phosphite, e.g., tris(2,4-di-t-amylphenyl)phosphite, preferably is present in an amount of from 0.1 to 20 wt. %, e.g., from 0.3 to 5 wt. %, or from 0.5 to 1 wt. %. If present, the bis(dialkylaryl)monoalkylaryl phosphites, e.g., bis(2,4-di-t-amylphenyl)-4-t-amylphenyl phosphite, preferably is present in an amount of from 2 to 20 wt. %, e.g., from 4 to 20 wt. %, or from 5 to 10 wt. %. Unless otherwise indicated, weight percent (wt. %) is based on the total weight of all phosphite components in the phosphite composition.

In terms of weight ratios for these phosphite compositions, the phosphite composition optionally has a weight ratio of tris(monoalkylaryl)phosphites to the combination of bis(monoalkylaryl)dialkylaryl phosphites, (dialkylaryl)monoalkylaryl phosphites and tris(dialkylaryl)phosphites of from 1:4 to 7:3, e.g., from 2:5 to 3:2, or from 3:5 to 6:5. The phosphite composition optionally has a weight ratio of bis(monoalkylaryl)dialkylaryl phosphites to the combination of tris(monoalkylaryl)phosphites, bis(dialkylaryl)monoalkylaryl phosphites and tris(dialkylaryl)phosphites of from 1:6 to 3:2, e.g., from 1:3 to 1:1, or from 1:2 to 3:2. The phosphite composition optionally has a weight ratio of bis(dialkylaryl)monoalkylaryl phosphites to the combination of tris(monoalkylaryl)phosphites, bis(monoalkylaryl)dialkylaryl phosphites, and tris(dialkylaryl)phosphites of from 1:50 to 2:5, e.g. from 1:30 to 1:5, or from 1:20 to 1:9. The phosphite composition optionally has a weight ratio of tris(dialkylaryl)phosphites to the combination of bis(monoalkylaryl)dialkylaryl phosphites, bis(dialkylaryl)monoalkylaryl phosphites and tris(monoalkylaryl)phosphites of from 1:10,000 to 2:5, e.g. from 1:5,000 to 1:20, or from 1:1000 to 1:100.

In a preferred embodiment, the phosphite composition comprises at least two of a tris(di-$C_3$-$C_5$ alkylaryl)phosphite, a tris($C_3$-$C_5$ alkylaryl)phosphite, a bis(di-$C_3$-$C_5$ alkylaryl) $C_3$-$C_5$ alkylaryl phosphite, and a bis($C_3$-$C_5$ alkylaryl) di-$C_3$-$C_5$ alkylaryl phosphite. Preferably the composition comprises each of the those phosphites in the following amounts: 30-50 wt % of a tris(di-$C_3$-$C_5$ alkylaryl)phosphite, 30-50 wt % of a tris($C_3$-$C_5$ alkylaryl)phosphite, 5-15 wt % of a bis(di-$C_3$-$C_5$ alkylaryl) $C_3$-$C_5$ alkylaryl phosphite, and less than 4 wt % of a bis($C_3$-$C_5$ alkylaryl) di-$C_3$-$C_5$ alkylaryl phosphite.

As indicated above, the phosphite compositions of the invention include a composition of phosphite compounds having aryl moieties that are monoalkylated and dialkylated.

Preferably, the phosphite composition has a low level or is substantially free of phenolics (e.g., phenols, cresols or xylenols), whether alkylated or unalkylated, which is referred to herein as "free phenolics" when contained in the phosphite composition. In terms of amounts, the phosphite composition preferably comprises less than 5 wt. %, e.g., less than 3 wt. %, or less than 1 wt. %, of free phenolics, based on the total weight of the phosphite composition. Any free phenolics, for example, may be removed by distillation. Extremely low levels of free phenolics may be achieved, for example, by employing a wiped-film molecular (Short-Path) still, wiped film evaporator (WFE), thin film evaporator, or similar equipment. In terms of amounts, the phosphite composition may comprise less than 0.5 wt. %, e.g., less than 0.2 wt. %, or less than 0.1 wt. %, of free phenolics, based on the total weight of the phosphite composition.

In other embodiments, a minor amount of free phenolics may be beneficial, for example, as a viscosity reducing agent. Thus, in one embodiment, the phosphite composition comprises a minor amount of free phenolics, e.g., from 1 to 4 weight percent, e.g., from 2 to 3 weight percent, based on the total weight of the phosphite composition.

In addition, the phosphite composition is preferably substantially free of phosphite compounds having unsubstituted aryl moieties, e.g., triphenylphosphites, bis(phenyl)alkylphenyl phosphites or bis(alkylphenyl)phenyl phosphites. In terms of amounts, the phosphite composition preferably comprises less than 2 wt. %, e.g., less than 1 wt. %, or less than 0.5 wt. %, phosphite compounds having at least one unsubstituted aryl moiety, based on the total weight of the phosphite composition.

In some preferred embodiments, the phosphite composition includes one or more hydrolytic stabilizers. Preferred stabilizers include amines of the structure:

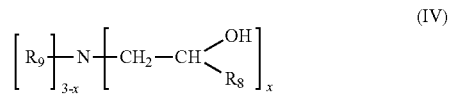

(IV)

wherein x is 1, 2, or 3; $R_8$ is selected from the group consisting of hydrogen, and straight or branched $C_1$-$C_6$ alkyl, and $R_9$ is selected from the group consisting of straight or branched $C_1$-$C_{30}$ alkyl. Preferably $R_8$ is selected from the group consisting of straight or branched $C_1$-$C_4$ alkyl, e.g., methyl or ethyl. Preferably $R_9$ is selected from the group consisting of straight or branched $C_5$-$C_{20}$ alkyl, e.g., straight or branched $C_{10}$-$C_{20}$ alkyl or straight or branched $C_{12}$-$C_{18}$ alkyl. In one embodiment, x is 1 and $R_9$ is straight or branched $C_5$-$C_{20}$ alkyl, e.g., $C_{12}$-$C_{18}$ alkyl. In one embodiment, x is 2 and $R_9$ is straight or branched $C_{10}$-$C_{20}$ alkyl, e.g., $C_{12}$-$C_{18}$ alkyl.

In one aspect the amine is selected from the group consisting of triethanolamine, triisopropanolamine, diethanolamine, diisopropanolamine, and tetraisopropanolethylenediamine.

In another aspect the amine is selected from the group consisting of octyl-bis(2-ethanol)amine, nonyl-bis(2-ethanol)amine, decyl-bis(2-ethanol)amine, undecyl-bis(2-ethanol)amine, dodecyl-bis(2-ethanol)amine, tridecyl-bis(2-ethanol)amine, tetradecyl-bis(2-ethanol)amine, pentadecyl-bis(2-ethanol)amine, hexadecyl-bis(2-ethanol)amine, heptadecyl-bis(2-ethanol)amine, octadecyl-bis(2-ethanol)amine, octyl-bis(2-propanol)amine, nonyl-bis(2-propanol)amine, decyl-bis(2-propanol)amine, undecyl-bis(2-propanol)amine, dodecyl-bis(2-propanol)amine, tridecyl-bis(2-propanol)amine, tetradecyl-bis(2-propanol)amine, pentadecyl-bis(2-propanol)amine, hexadecyl-bis(2-propanol)amine, heptadecyl-bis(2-propanol)amine, octadecyl-bis(2-propanol)amine, and isomers thereof. Commercially available amines include Armostat™ 300 and Armostat 1800 manufactured by Akzo Nobel Polymers.

Additional hydrolytic stabilizers include epoxies such as epoxidized soybean oil (ESBO) commercially available as Drapex™ 39, Drapex 392, Drapex 4.4, and Drapex 6.8 (Chemtura Corp.) or polycarbodiimides, commercially available as Stabaxol™ P (Rhein Chemie).

The amine may be present in an amount of from 0.01 to 5 wt. %, e.g., from 0.1 to 1.5 wt. %, or from 0.2 to 0.8 wt. %, based on the total weight of the phosphite composition.

As indicated above, the phosphite composition is a liquid at ambient conditions. As used herein, by "liquid" it is meant that the phosphite composition remains liquid after repeated freeze/thaw cycles as opposed to "meta-stable liquids" that do not remain liquids after such cycles. A freeze/thaw cycle is defined as follows: 1) An ambient temperature composition is stirred for 0.5 hours; 2) The stirred composition is then refrigerated at about 5° C. for three days; and 3) The refrigerated composition is then brought to ambient temperature and held at ambient for 3 days. Upon completion of step 3, the composition is checked for solids content, e.g., crystallization. Completion of steps 1-3 defines one freeze/thaw cycle.

As noted above, it is a feature of the present invention that the phosphite composition is in liquid physical form at room temperature. This is clearly surprising, given that the prior art teaches several examples of solid phosphite compositions, the components of which are separately solids at ambient condition, (See JP 59030842; WO 9303092; CA 2,464,551). In the present invention, in contrast, the phosphite compositions are liquid even though the individual components are solid. Table 4 provides the melting points of several different phosphites within the scope of the present invention.

TABLE 4

| Phosphite | Melting Point |
| --- | --- |
| tris(4-t-butylphenyl)phosphite | 75-76° C. |
| tris(2,4-di-t-butylphenyl)phosphite | 181-184° C. |
| bis(4-t-butylphenyl)-2,4-di-t-butylphenyl phosphite | 63-65° C. |
| bis(2,4-di-t-butylphenyl)-4-t-butylphenyl phosphite | 100-103° C. |
| tris(4-t-amylphenyl)phosphite | 52-54° C. |
| tris(2,4-di-t-amylphenyl)phosphite | 103° C. |

The viscosity of the phosphite composition may vary depending on the relative amounts of the various phosphite compounds contained therein. In some exemplary embodiments, the phosphite composition has a viscosity less than 11,000 cSt, e.g., less than 7,300 cSt, less than 5,000 cSt, less than 3,000 cSt, or less than 2850 cSt, these viscosities being measured at 30° C. In terms of ranges, viscosity of the composition may range from 1 cSt to 15,000 cSt, from 100 cSt to 12,000 cSt, from 500 cSt to 10,000 cSt, from 500 cSt to 6,500 cSt, from 500 cSt to 5,000 cSt, from 500 cSt to 3,000 cSt, from 1,000 cSt to 4,000 cSt, from 1,500 cSt to 3,500 cSt, from 2,000 cSt to 3,000 cSt, or from 2,000 to 2,800 cSt, these viscosities being measured at 30° C.

Stabilizers

As discussed above, a stabilizing amount or effective amount of the phosphite composition of the invention may be used as a secondary antioxidant for various types of polymers. As used herein, by "stabilizing amount" and an "effective amount" it is meant when the polymer composition containing the phosphite compositions of the invention shows improved stability in any of its physical or color properties in comparison to an analogous polymer composition which does not include a phosphite composition of the invention. Examples of improved stability include improved stabilization against, for example, molecular weight degradation, color degradation, and the like from, for example, melt processing, weathering, and/or long term field exposure to air, heat, light, and/or other elements. In one example, improved stability is obtained in the form of one or both of lower initial color as measured by yellowing index (YI) and melt flow rate of the molten polymer or additional resistance to weathering, as measured, for example, by initial yellowing index, or by resistance to yellowing and change in color, when compared to a composition without the stabilizer additive.

The additives and stabilizers described herein are preferably present in an amount effective to improve composition stability. When one of the aforementioned phosphite compositions is utilized, the composition is generally present in an amount from about 0.001 to about 5 wt. %, e.g., from about 0.0025 to about 2 wt. % or from about 0.005 to about 1 wt. %, based on the total weight of the polymer including the weight of the phosphite composition and any other stabilizers or additives. The phosphite compositions of this invention stabilize resins especially during high temperature processing with relatively little change in melt index and/or color, even after multiple extrusions.

The invention further relates to a stabilized thermoplastics, comprising a base polymer (e.g., polymer resin) and any of the aforementioned phosphite compositions of the invention. The polymer resin may be a polymer such as a polyolefin, and the liquid phosphite composition may be used with a costabilizer, for example, hindered phenolics, aromatic amines, hydroxylamines, lactones, and thioethers. Thus, the thermoplastic that is stabilized by the phosphite compositions of the present invention may optionally contain one or more additional stabilizers or mixtures of stabilizers selected from the group consisting of the phenolic antioxidants, hindered amine light stabilizers (HALS), the ultraviolet light absorbers, phosphites, phosphonites, alkaline metal salts of fatty acids, hydrotalcites, metal oxides, epoxydized soybean oils, the hydroxylamines, the tertiary amine oxides, lactones, thermal reaction products of tertiary amine oxides, and the thiosynergists.

In one embodiment, the amount of each component in the stabilizing composition, based on the total weight percent of the polymer or polymeric resin, is shown in Table 5.

TABLE 5

| Component | Range | Preferred Range |
| --- | --- | --- |
| Liquid phosphite compositions | 0.001-5.0 wt % | 0.005-1.0 wt % |
| Primary antioxidant | 0-5.0 wt % | 0.005-2.0 wt % |
| UV or light stabilizers | 0-3.0 wt % | 0.001-2.0 wt % |
| Metal deactivators | 0-3.0 wt % | 0.001-2.0 wt % |
| Other secondary antioxidants | 0-3.0 wt % | 0.001-2.0 wt % |
| Peroxide scavengers | 0-3.0 wt % | 0.001-2.0 wt % |
| Polyamide stabilizers | 0-3.0 wt % | 0.001-2.0 wt % |
| Basic co-stabilizers | 0-3.0 wt % | 0.001-2.0 wt % |
| Nucleating or clarifying agents | 0-3.0 wt % | 0.001-2.0 wt % |
| Aminoxy propanoate | 0-3.0 wt % | 0.001-2.0 wt % |

The phosphite compositions of the invention or the resulting stabilized polymer compositions optionally also comprise primary antioxidants such as the following:

(i) Alkylated monophenols, for example: 2,6-di-tert-butyl-4-methylphenol, 2-tert-butyl - 4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2,6-bis(α-methylbenzyl)-4-methylphenol, 2-(α-methylcyclohexyl)-4,6-dimethylphenol, 2,6-dioctadecyl-4- methylphenol, 2,4,6,-tricyclohexyphenol, and 2,6-di-tert-butyl-4-methoxymethylphenol. Commercially available alkylated monophenols include Lowinox™ 624 and Naugard™ 431 made by Chemtura Corp. Other phenols are commercially available such as BHEB.

(ii) Alkylated hydroquinones, for example, 2,6-di-tert-butyl-4-methoxyphenol, 2,5-di-tert-butyl-hydroquinone, 2,5--di-tert-amyl-hydroquinone, and 2,6-diphenyl-4octadecyloxyphenol. Commercially available alkylated hydroquinones include Lowinox AH25 made by Chemtura.

(iii) Hydroxylated thiodiphenyl ethers, for example, 2,2'-thio-bis-(6-tert-butyl-4-methylphenol), 2,2'-thio-bis-(4-octylphenol), 4,4'-thio-bis-(6-tert-butyl-3-methylphenol), and 4,4'-thio-bis-(6-tert-butyl-2-methyphenol). Commercially available hydroxylated thiodiphenyl ethers include Lowinox TBM6, and Lowinox TBP6 made by Chemtura.

(iv) Alkylidene-bisphenols, for example, 2,2'-methylene-bis-(6-tert-butyl-4-methylphenol), 2,2'-methylene-bis-(6-tert-butyl-4-ethylphenol), 2,2'-methylene-bis-(4-methyl-6-(α-methylcyclohexyl)phenol), 2,2'-methylene-bis-(4-methyl-6-cyclohexylphenol), 2,2'-methylene-bis-(6-nonyl-4-methylphenol), 2,2'-methylene-bis-(6-nonyl-4-methylphenol), 2,2'-methylene-bis-(6-(α-methylbenzyl)-4-nonylphenol), 2,2'-methylene-bis-(6-(alpha,alpha-dimethylbenzyl) -4-nonyl-phenol), 2,2'-methylene-bis-(4,6-di-tert-butylphenol), 2,2'-ethylidene-bis-(6-tert-butyl-4-isobutylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenol)butane, 1,1-bis(2-methyl-4-hydroxy-5-tert-butylphenyl)butane, 2,2'-isobutylidene-bis(4,6-dimethylphenol), 2,6-di-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy-2-methylphenyl)-3-dodecyl-mercaptobutane, ethyleneglycol-bis-(3,3,-bis-(3'-tert-butyl-4'-hydroxyphenyl)-butyrate)-di-(3-tert-butyl-4-hydroxy-5-methylphenyl)-dicyclopentadiene, and di-(2-(3'-tert-butyl-2'hydroxy-5'methyl-benzyl)-6-tert-butyl-4-methylphenyl)terephthalate. Commercially available alkylidene-bisphenols include Lowinox 22M46, Lowinox WSP, Lowinox 44B25, Naugard 536, Naugawhite™, and Lowinox 22IB46 made by Chemtura.

(v) Benzyl compounds, for example, 1,3,5-tris-(3,5-di-tert-butyl-4-hydroxybenzyl)-2,4,6-trimethylbenzene, bis-(3,5-di-tert-butyl-4-hydroxybenzyl)sulfide, isooctyl 3,5-di-tert-butyl-4-hydroxybenzyl-mercapto-acetate, bis-(4-tert-butyl-3-hydroxy-2,6-dimethylbenzyl)dithiol-terephthalate, 1,3,5-tris-(3,5-di-tert-butyl-4 hydroxybenzyl)isocyanurate, 1,3,5-tris-(4-tert-butyl-3-hydroxy-2,6-dimethylbenzyl) isocyanurate, 1,3,5-tris(4-t-butyl-3-hydroxy-2,6-dimethylbenzyl)-1,3,5-Triazine-2,4,6-(1H,3H,5H)-trione, dioctadecyl-3,5-di-tert-butyl-4-hydroxybenzyl-phosphonate, calcium salt of monoethyl 3,5-di-tert-butyl-4-hydroxybenzylphosphonate, 1,3,5-tris-(3,5-dicyclohexyl-4-hydroxybenzyl)isocyanurate. Commercially available benzyl compounds include Anox™ IC-14, Anox 330 and Lowinox 1790 made by Chemtura.

(vi) Acylaminophenols, for example, 4-hydroxylauric acid anilide, 4-hydroxy-stearic acid amilide, 2,4-bis-octylmercapto-6-(3,5-tert-butyl-4-hydroxyanilino)-s-triazine, and octyl-N-(3,5-di-tert-butyl-4-hydroxyphenyl)-carbamate.

(vii) Esters of beta-(3,5-di-tert-butyl-4-hydroxyphenol)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethylisocyanurate, thiodiethyleneglycol, di-hydroxyethyl oxalic acid diamide. Such phenols also include tetrakis [methylene {3,5-di-tert-butyl-4-hydroxycinnamate}]methane. Commercially available esters include Anox 20, Anox 1315, Lowinox GP45, Naugalube 38, Naugalube 531, Anox PP18, Naugard PS48 and Naugard XL-1 made by Chemtura.

(viii) Thio esters of beta-(5-tert-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, dihydroxyethyl oxalic acid diamide. Commercially available thio esters include Naugalube™ 15 and Anox 70 made by Chemtura.

(ix) Amides of beta-(3,5-di-tert-butyl-4-hydroxyphenol)-propionic acid for example, N,N'-di-(3,5-di-tert-butyl-4-hydroxyphenylpropionyl)-hexammethylen-diamine, N,N'-di-(3,5-di-tert-butyl-4-hydroxyphenylpropionyl) trimethylenediamine, N,N'-di-(3,5-di-tert-butyl-4-hydroxyphenylpropionyl)-hydrazine, N,N'-Hexamethylene bis[3-(3,5-di-t-butyl-4-hydroxyphenyl)propionamide, and 1,2-Bis(3,5-di-tert-butyl-4-hydroxyhydrocinnamoyehydrazine. Commercially available amides include Lowinox HD98 and Lowinox MD24 made by Chemtura.

(x) Other phenolic antioxidants include the following phenols. Polymeric phenols such as the reaction product of 4-methylphenol with dicyclopentadiene and isobutylene, commercially available as Lowinox CPL; Chemtura. Alkylidene-poly-phenols, such as 1,3 tris(3-methyl-4-hydroxyl-5-t-butyl-phenyl)-butane (Lowinox CA22; Chemtura). Thio phenols such as 2,6-di-tert-butyl-4-(4,6-bis(octylthio)-1,3,5-triazin-2-ylamino)phenol (Irganox™ 565; Ciba), 4,6-bis(octylthiomethyl)-o-cresol (Irganox 1520; Ciba); 4,6-bis(dodecylthiomethyl)-o-cresol (Irganox 1726; Ciba). Hydroxyl amines, such as bis(octadecyl)hydroxylamine (Irgastab™ FS 042; Ciba). Ester phenols include bis[3,3-bis(4-hydroxy-3-tert-butyl phenyl)butanoic acid]glycol ester (Hostanox™ 03; Clariant Chemicals). Still other phenols include 2-[1-(2-hydroxy-3,5-di-tert-pentylphenyl)ethyl]-4,6-di-tert-pentylphenyl acrylate (Sumilizer GS; Sumitomo Chemical).

In one embodiment, the stabilizing composition comprises one phenolic selected from the group consisting of tetrakismethylene(3,5-di-t-butyl-4-hydroxylhydrocinnamate)methane (Anox 20), 1,3,5-tris(3,5-di-t-butyl-4-hydroxybenzyl) isocyanurate (Anox IC-14), 1,3,5-tris(4-tert.-butyl-3-hydroxy-2,6-dimethylbenzyl)-1,3,5-triazine-2,4,6-(1H,3H, 5H)-trione (Lowinox 1790), octyl-3-(3,5-di-t-butyl-4-hydroxyphenyl)propionate (Anox PP18), bis(octadecyl) hydroxylamine (Irgastab FS-042), 1,3,5-trimethyl-2,4,6-tris (3,5-di-tert-4-hydroxybenzyl) benzene (Anox 330), 2,6-bis (α-methylbenzyl)-4-methylphenol (Naugalube 431), 3,5-bis (1,1-dimethylethyl)-4-hydroxy-benzenepropanoic acid (Anox 1315), 2,6-di-t-butyl-4-ethyl-phenol (BHEB), and mixtures thereof, and the liquid phosphite composition defined herein.

The phosphite compositions and/or the resulting stabilized polymeric compositions optionally also comprise one or more UV absorbers and/or light stabilizers, such as the following:

(i) 2-(2'-hydroxyphenyl)-benzotriazoles, for example, the 5'-methyl-, 3'5'-di-tert-butyl-, 3'5'-di-tert-amyl-, 5'-tert-butyl-, 5'-tert-amyl-, 5'(1,1,3,3-tetramethylbutyl)-, 5-chloro-3', 5'-di-tert-butyl-, 5-chloro-3'-tert-butyl-5'-methyl-, 3'-sec-butyl-5'-tert-butyl-,4'-octoxy, 3',5'-ditert-amyl-3',5'-bis-(α,α-dimethylbenzyl)-derivatives. Commercially available 2-(2'-hydroxyphenyl)-benzotriazoles include Lowilite™ 26, Lowilite 27, Lowilite 28, Lowilite 29, Lowilite 35, Lowilite 55, and Lowilite 234 made by Chemtura.

(ii) 2-Hydroxy-benzophenones, for example, the 4-hydroxy, 4-methoxy-, 4-octoxy, 4-decyloxy-, 4-dodecyloxy-, 4-benzyloxy-, 2,4-dihydroxy-, 4,2',4'-trihydroxy- and 2'-hydroxy-4,4'-dimethoxy-derivative. Exemplary 2-hydroxy-benzophenones include 2-hydroxy-4-methoxybenzophenone, 2-hydroxy-4-ethoxybenzophenone, 2,4-dihydroxybenzophenone, and 2-hydroxy-4-propoxybenzophenone. Commercially available 2-(2'-hydroxyphenyl)-benzotriazoles include Lowilite 20, Lowilite 22, Lowilite 20S, and Lowilite 24 made by Chemtura.

(iii) Esters of substituted and unsubstituted benzoic acids for example, phenyl salicylate, 4-tert-butylphenyl-salicilate, octylphenyl salicylate, dibenzoylresorcinol, bis-(4-tert-butylbenzoyl)-resorcinol, benzoylresorcinol, 2,4-di-tert-butylphenyl-3,5-di-tert-butyl-4-hydroxybenzoate and hexadecyl-3,5-di-tert-butyl-4-hydroxybenzoate.

(iv) UV absorbers and light stabilizers may also comprise acrylates, for example, alpha-cyano-beta, beta-diphenylacrylic acid-ethyl ester or isooctyl ester, alpha-carbomethoxy-cinnamic acid methyl ester, alpha-cyano-beta-methyl-p-methoxy-cinnamic acid methyl ester or butyl ester, alpha-carbomethoxy-p-methoxy-cinnamic acid methyl ester, N-(beta-carbomethoxy-beta-cyano-vinyl)-2-methyl-indoline.

(v) Nickel compounds are also suitable UV absorbers and light stabilizers. Exemplary nickel compounds include nickel complexes of 2,2'-thio-bis(4-(1,1,1,3-tetramethylbutyl)-phenol), such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl, or butyl ester, nickel complexes of ketoximes such as of 2-hydroxy-4-methyl-penyl undecyl ketoxime, nickel complexes of 1-phenyl-4-lauroyl-5-hydroxy-pyrazole, optionally with additional ligands. Commercially available nickel compounds include Lowilite Q84 (2,2'-Thiobis(4-tert-octyl-phenolato))-N-butylamine-Nichel(11) made by Chemtura.

(vi) Sterically hindered amines may be used as UV absorbers and light stabilizers. Sterically hindered amines, for example bis(2,2,6,6-tetramethylpiperidyl)-sebacate, bis-(1, 2,2,6,6-pentamethylpiperidyl)-sebacate, n-butyl-3,5-di-tert-butyl-4-hydroxybenzyl malonic acid bis(1,2,2,6,6-pentamethylpiperidyl) ester, condensation product of 1-hydroxyethyl-2,2,6,6-tetramethyl-4-hydroxy-piperidine and succinic acid, condensation product of N,N'-(2,2,6,6-tetramethylpiperidyl)-hexamethylendiamine and 4-tert-octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetra-carbonic acid, 1,1'(1,2-ethanediyl)-bis-(3,3,5,5-tetramethylpiperazinone). Such amines include hydroxylamines derived from hindered amines, such as di(1-hydroxy-2,2,6,6-tetramethylpiperidin-4-yl)sebacate: 1-hydroxy 2,2,6,6-tetramethyl-4-benzoxypiperidine; 1-hydroxy-2,2,6,6-tetramethyl-4-(3,5-di-tert-butyl-4-hydroxy hydrocinnamoyloxy)-piperdine; and N-(1-hydroxy-2,2,6,6-tetramethyl-piperidin-4-yl)-epsiloncaprolactam. Commercially available hindered amines include Lowilite 19, Lowilite 62, Lowilite 77, Lowilite 92 and Lowilite 94 made by Chemtura.

(vii) Oxalic acid diamides, for examples, 4,4'-dioctyloxy-oxanilide, 2,2'-di-octyloxy-5',5'-di-tert-butyloxanilide, 2,2'-di-dodecyloxy-5',5'di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'ethyl-5,4-di-tert-butyloxanilide and mixtures of o-and p-methoxy-as well as of o- and p-ethoxy-disubstituted oxanilides.

The polymer resins and phosphite compositions of the invention may also include one or more additional additives, including, for example, one or more of the following:

(i) Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydrophenylpropionyl)-hydrazine, salicyloylamino-1,2,4-triazole, bis-benzyliden-oxalic acid dihydrazide.

(ii) Additional secondary antioxidants such as additional phosphites and/or phosphonites, for example, triphenyl phosphite, diphenylalkyl phosphites, phenyldialkyl phosphites, tris(nonyl-phenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite tristearyl sorbitol triphosphite, bis (2,4-di-cumylphenyl)pentaerythritol diphosphite, and tetrakis(2,4-di-tert-butylphenyl)4,4'-biphenylene diphosphonite. Commercially available secondary antioxidants include Naugalube TPP, Alkanox™ 240, Ultranox™ 626, Naugard P, Weston™ 399, Weston TNPP, Weston 430, Weston 618F, Weston 619F, Weston DPDP, Weston DPP, Weston PDDP, Weston PTP, Weston TDP, Weston TLP, Weston TPP, and Weston TLTTP (trilauryl trithio phosphite) made by Chemtura; Doverphos™ 4, Doverphos 4-HR, Doverphos 4-HR Plus, Doverphos HiPure 4, and Doverphos S-9228 made by Dover Chemical; and Hostanox PEPQ made by Clariant Chemicals.

(iii) Peroxide scavengers, for example, esters of betathio-dipropionic acid, for example the lauryl, stearyl, myristyl or tridecyl esters, mercaptobenzimidazole or the zinc salt of 2-mercaptobenzimidazole, zinc-dibutyldithiocaramate, dioctadecyldisulfide, pentaerythritoltetrakis-(beta-dodecylmercapto)-propionate.

(iv) Polyamide stabilizers, for example copper salts in combination with iodides and/or phosphorus compounds and salts of divalent manganese may also be included in the polymer resin and/or phosphite composition.

(v) Basic co-stabilizers, for example, melamine, polyvinylpyrrolidone, dicyandiamide, triallyl cyanurate, urea derivatives, hydrazine derivatives, amines, polyamides, polyurethanes, hydrotalcites, alkali metal salts and alkaline earth metal salts of higher fatty acids, for example, Ca stearate, calcium stearoyl lactate, calcium lactate, Zn stearate, Zn octoate, Mg stearate, Na ricinoleate and K palmirate, antimony pyrocatecholate or zinc pyrocatecholate. Commercially available co-stabilizers include Mark™ 6045, Mark 6045ACM, Mark 6055, Mark 6055ACM, Mark 6087ACM, Mark 6102, Mark CE 345, Mark CE 350, and Mark CE 387, made by Chemtura; and DHT-4A™ made by Kisuma Chemicals.

(vi) Nucleating and clarifying agents, for example, metal salts of 4-tert butylbenzoic acid, adipic acid, diphenylacetic acid, sorbitol and derivatives thereof, sodium benzoate, and benzoic acid.

(vii) Aminoxy propanoate derivatives such as methyl-3-(N, N-dibenzylaminoxy)propanoate; ethyl-3-(N,N-dibenzylaminoxy)propanonoate; 1,6-hexamethylene-bis(3-N,N-dibenzylaminoxy)proponoate); methyl-(2-(methyl)-3(N,N-dibenzylaminoxy)propanoate); octadecyl-3-(N,N-dibenzylaminoxy)propanoic acid; tetrakis (N,N-dibenzylaminoxy)ethyl carbonyl oxymethy)methane; octadecyl-3-(N,N-diethylaminoxy)-propanoate; 3-(N,N- dibenzylaminoxy)propanoic acid potassium salt; and 1,6-hexamethylene bis(3-(N-allyl-N-dodecyl aminoxy)propanoate).

(viii) Other additives, for example, plasticizers, lubricants, emulsifiers, pigments, optical brighteners, flameproofing agents, anti-static agents, blowing agents and thiosynergists such as dilaurythiodipropionate or distearylthiodipropionate.

Optionally the polymer or polymeric resins may include from 5-50 wt %, e.g., 10-40 wt % or 15-30 wt % fillers and reinforcing agents, for example, calcium carbonate, silicates, glass fibers, asbestos, talc, kaolin, mica, barium sulfate, metal oxides and hydroxides, carbon black and graphite.

The invention further pertains to a stabilized polymer, wherein one component comprises a liquid phosphite composition of the present invention and the other a polymer, such as a polyolefin, polyvinyl chloride, etc., or polymeric resins.

The polymer stabilized by such liquid phosphite compositions may be any polymer known in the art, such as polyolefin homopolymers and copolymers, thermoplastics, rubbers, polyesters, polyurethanes, polyalkylene terephthalates, polysulfones, polyimides, polyphenylene ethers, styrenic polymers and copolymers, polycarbonates, acrylic polymers, polyamides, polyacetals, halide-containing polymers, and biodegradable polymers. Mixtures of different polymers, such as polyphenylene ether/styrenic resin blends, polyvinyl chloride/ABS or other impact modified polymers, such as methacrylonitrile and α-methylstyrene containing ABS, and polyester/ABS or polycarbonate/ABS and polyester plus some other impact modifier may also be used. Such polymers are available commercially or may be made by means well known in the art. However, the stabilizer compositions of the invention are particularly useful in thermoplastic polymers, such as polyolefins, polycarbonates, polyesters, polyphenylene ethers and styrenic polymers, due to the extreme temperatures at which thermoplastic polymers are often processed and/or used.

The polymers used in combination with liquid phosphite compositions of the present invention are produced using a variety of polymerization processes including solution, high-pressure, slurry and gas phase using various catalysts including Ziegler-Natta, single-site, metallocene or Phillips-type catalysts. Non-limiting polymers useful with the liquid phosphite compositions include ethylene based polymers such as linear low density polyethylene, elastomers, plastomers, high density polyethylene, substantially linear long chain branched polymers, and low density polyethylene; and propylene based polymers such as polypropylene polymers including atactic, isotactic, and syndiotactic polypropylene polymers, and propylene copolymers such as propylene random, block or impact copolymers.

The polymers, typically ethylene based polymers, have a density in the range of from 0.86 g/cc to 0.97 g/cc, preferably in the range of from 0.88 g/cc to 0.965 g/cc, more preferably in the range of from 0.900 g/cc to 0.96 g/cc, even more preferably in the range of from 0.905 g/cc to 0.95 g/cc, yet even more preferably in the range from 0.910 g/cc to 0.940 g/cc, and most preferably greater than 0.915 g/cc, preferably greater than 0.920 g/cc, and most preferably greater than 0.925 g/cc. The polymers produced by the process of the invention typically have a molecular weight distribution, a weight average molecular weight to number average molecular weight (Mw/Mn) of greater than 1.5 to about 15, particularly greater than 2 to about 10, more preferably greater than about 2.2 to less than about 8, even more preferably from about 2.2 to less than 5, and most preferably from 2.5 to 4. The ratio of Mw/Mn can be measured by gel permeation chromatography techniques well known in the art. The polymers of the present invention in one embodiment have a melt index (MI) or (I2) as measured by ASTM-D-1238-E in the range from 0.01 dg/min to 1000 dg/min, more preferably from about 0.01 dg/min to about 100 dg/min, even more preferably from about 0.1 dg/min to about 50 dg/min, and most preferably from about 0.1 dg/min to about 10 dg/min. The polymers of the invention in one embodiment have a melt index ratio (I21/I2) (I21 is measured by ASTM-D-1238-F) of from 10 to less than 25, more preferably from about 15 to less than 25. The polymers of the invention in a preferred embodiment have a melt index ratio (I21/I2) (I21 is measured by ASTM-D-1238-F) of from preferably greater than 25, more preferably greater than 30, even more preferably greater that 40, still even more preferably greater than 50 and most preferably greater than 65.

Polymers used with liquid phosphites compositions of the invention are useful in such forming operations as film, sheet, and fiber extrusion and co-extrusion as well as blow molding, injection molding and rotary molding. Films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers include melt spinning, solution spinning and melt blown fiber operations for use in woven or non-woven form to make filters, diaper fabrics, medical garments, geotextiles, etc. Extruded articles include medical tubing, wire and cable coatings, geomembranes, and pond liners. Molded articles include single and multi-layered constructions in the form of bottles, tanks, large hollow articles, rigid food containers and toys, etc. In addition to the above, the liquid phosphite compositions are used in various rubber based products such as tires, barriers and the like.

In one embodiment, the liquid phosphite compositions are suitable and/or approved for use in polymers, preferably polyolefins, that are used in contact with beverages, foods and other human consumables.

Polymers of monoolefins and diolefins, for example polypropylene, polyisobutylene, polybutene-1, polymethylpentene-1, polyisoprene, or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may be used. Mixtures of these polymers, for example, mixtures of polypropylene with polyisobutylene, polypropylene with polyethylene (for example PP/HDPE, PP/LDPE) and mixtures of different types of polyethylene (for example LDPE/HDPE), may also be used. Also useful are copolymers of monoolefins and diolefins with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/isobutylene, ethylene/butane-1, propylene/butadiene, isobutylene, isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidene-norbornene; as well as mixtures of such copolymers and their mixtures with polymers mentioned above, for example polypropylene/ethylene propylene-copolymers, LDPE/EVA, LDPE/EAA, LLDPE/EVA, and LLDPE/EAA.

The olefin polymers may be produced by, for example, polymerization of olefins in the presence of Ziegler-Natta catalysts optionally on supports such as, for example, MgCl$_2$, chromium 20 salts and complexes thereof, silica, silica-alumina and the like. The olefin polymers may also be produced utilizing chromium catalysts or single site catalysts, e.g., metallocene catalysts such as, for example, cyclopentadiene complexes of metals such as Ti and Zr. As one skilled in the art would readily appreciate, the polyethylene polymers used herein, e.g., LLDPE, can contain various comonomers such as, for example, 1-butene, 1-hexene and 1-octene comonomers.

The polymer may also include styrenic polymers, such as polystyrene, poly-(p-methylstyrene), 5 poly-(α-methylstyrene), copolymers of styrene or α-methylstyrene with dienes or acrylic derivatives, such as, for example, styrene/butadiene (SBR), styrene/acrylonitrile, styrene/alkyl methacrylate, styrene/maleic anhydride, styrene/maleimide, styrene/butadiene/ethyl acrylate, styrene/acrylonitrile/methylacrylate, mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene (SBS), styrene/isoprene/styrene (SIS), styrene/ethylene/butylene/styrene or styrene/ethylene/propylene/styrene.

Styrenic polymers may additionally or alternatively include graft copolymers of styrene or α-methylstyrene such as, for example, styrene on polybutadiene, styrene on polybutadiene-styrene or polybutadiene-acrylonitrile; styrene and acrylonitrile (or methacrylonitrile) on polybutadiene and copolymers thereof; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene-propylene-diene terpolymers, styrene and acrylonitrile on polyacrylates or polymethacrylates, styrene and acrylonitrile on acrylate/butadiene copolymers, as well as mixtures thereof with the styrenic copolymers indicated above.

Suitable rubbers include both natural rubber and synthetic rubbers, and combinations thereof. Synthetic rubbers include, but are not limited to, for example, thermoplastic rubbers, ethylene/alpha-olefin/non-conjugated polyene (EPDM) rubbers, ethylene/alpha-olefin (EPR) rubbers, styrene/butadiene rubbers, acrylic rubbers, nitrile rubbers, polyisoprene, polybutadiene, polychloroprene, acrylonitrile/butadiene (NBR) rubbers, polychloroprene rubbers, polybutadiene rubbers, isobutylene-isoprene copolymers, etc. Thermoplastic rubbers include SIS, solution and emulsion SBS, etc.

Nitrile polymers are also useful in the polymer composition of the invention. These include homopolymers and copolymers of acrylonitrile and its analogs, such as polymethacrylonitrile, polyacrylonitrile, acrylonitrile/butadiene polymers, acrylonitrile/alkyl acrylate polymers, acrylonitrile/alkyl methacrylate/butadiene polymers, and various ABS compositions as referred to above in regard to styrenics.

Polymers based on acrylic acids, such as acrylic acid, methacrylic acid, methyl methacrylic acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide and methacrylamide may also be used.

Halogen-containing polymers may also be stabilized with the phosphite mixtures of the present invention. These include polymers such as polychloroprene, epichlorohydrin homo-and copolymers, polyvinyl chloride, polyvinyl bromide, polyvinyl fluoride, polyvinylidene chloride, chlorinated polyethylene, chlorinated polypropylene, fluorinated polyvinylidene, brominated polyethylene, chlorinated rubber, vinyl chloride-vinyl acetate copolymers, vinyl chloride-ethylene copolymer, vinyl chloride-propylene copolymer, vinyl chloridestyrene copolymer, vinyl chloride-isobutylene copolymer, vinyl chloride-vinylidene chloride copolymer, vinyl chloride-styrene-maleic anhydride terpolymer, vinyl chloride-styrene-acrylonitrile copolymer, vinyl chloride-butadiene copolymer, vinyl chloride isoprene copolymer, vinyl chloride-chlorinated propylene copolymer, vinyl chloride-vinylidene chloride-vinyl acetate terpolymer, vinyl chloride-acrylic acid ester copolymers, vinyl chloride-maleic acid ester copolymers, vinyl chloride-methacrylic acid ester copolymers, vinyl chloride-acrylonitrile copolymer and internally plasticized polyvinyl chloride.

Other useful polymers include homopolymers and copolymers of cyclic ethers, such as polyalkylene glycols, polyethylene oxide, polypropylene oxide or copolymers thereof with bisglycidyl ethers; polyacetals, such as polyoxymethylene and those polyoxymethylene which contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyester-carbonates; polysulfones, polyethersulfones and polyetherketones; and polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-2-(2,2,4(4-hydroxyphenyl)-propane)terephthalate and polyhydroxybenzoates as well as block copolyetheresters derived from polyethers having hydroxyl end groups.

Polyamides and copolyamides which are derived from bisamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylene bisamine and adipic acid; polyamides prepared from hexamethylene bisamine and isophthalic or/and terephthalic acid and optionally an elastomer as modifier, for example poly-2,4,4 trimethylhexamethylene terephthalamide or poly-m-phenylene isophthalamide may be useful. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols and polyamides or copolyamides modified with EPDM or ABS may be used.

In another embodiment, the polymer comprises a biodegradable polymer or compostable polymer. Biodegradable polymers are those in which the degradation results from the action of naturally occurring microorganisms, such as bacteria, fungi and algae. Compostable polymers undergoes degradation by biological processes during composting to yield CO$_2$, water, inorganic compounds and a biomass at a rate consistent with other compostable materials. Typically the biodegradable or compostable polymers are derived from plant sources and are synthetically produced. Examples of biodegradable or compostable polymers include poly(glycolic acid) (PGA), poly(lactic acid) (PLA), and co-polymers thereof. Biodegradable or compostable polymers may also be derived from a blend of starch of a plant and a conventional petroleum-based polymer. For example, the biodegradable polymer may be blended with a polyolefin.

Polyolefin, polyalkylene terephthalate, polyphenylene ether and styrenic polymers, and mixtures thereof are more preferred, with polyethylene, polypropylene, polyethylene terephthalate, polyphenylene ether homopolymers and copolymers, polystyrene, high impact polystyrene, polycarbonates and ABS-type graft copolymers and mixtures thereof being particularly preferred.

In one embodiment, the liquid phosphite compositions are added to stabilize natural and synthetic waxes, such as n-paraffin waxes, chloroparaffins, α-olefin waxes, microcrystalline waxes, polyethylene waxes, amide waxes, and Fisher-Tropsch waxes. These waxes may be suitable for making candles.

The instant stabilizers may readily be incorporated into the polymer by conventional techniques at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized compositions of the invention may optionally also contain from about 0.001 to about 5 wt. %, e.g., from about 0.0025 to about 2 wt. % or from about 0.05 to about 0.25 wt. %, of various conventional additives, such as those described previously, or mixtures thereof.

The stabilizers of this invention advantageously assist with the stabilization of polymer compositions especially in high temperature processing against changes in melt index and/or color, even though the polymer may undergo a number of extrusions. The stabilizers of the present invention may readily be incorporated into the polymer compositions by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer.

The compositions of the present invention can be prepared by a variety of methods, such as those involving intimate admixing of the ingredients with any additional materials desired in the formulation. Suitable procedures include solution blending and melt blending. Because of the availability of melt blending equipment in commercial polymer processing facilities, melt processing procedures are generally preferred. Examples of equipment used in such melt compounding methods include: co-rotating and counter-rotating extruders, single screw extruders, disc-pack processors and various other types of extrusion equipment. In some instances, the compounded material exits the extruder through small exit holes in a die and the resulting strands of molten resin are cooled by passing the strands through a water bath. The cooled strands can be chopped into small pellets for packaging and further handling.

All of the ingredients may be added initially to the processing system, or else certain additives may be pre-compounded with each other or with a portion of the polymer or polymeric resin to make a stabilizer concentrate. Moreover, it is also sometimes advantageous to employ at least one vent port to allow venting (either atmospheric or vacuum) of the melt. Those of ordinary skill in the art will be able to adjust blending times and temperatures, as well as component addition location and sequence, without undue additional experimentation.

While the stabilizers of this invention may be conveniently incorporated by conventional techniques into polymers before the fabrication thereof into shaped articles, it is also possible to apply the instant stabilizers by a topical application to the finished articles. Articles may comprise the instant stabilizer compounds and polymers and may be made into, for example, head lamp covers, roofing sheets, telephone covers, aircraft interiors, building interiors, computer and business machine housings, automotive parts, and home appliances. The articles may be made by extrusion, injection molding, roto-molding, compaction, and other methods. This may be particularly useful with fiber applications where the instant stabilizers are applied topically to the fibers, for example, by way of a spin finish during the melt spinning process. The phosphite compositions of the invention may have uses in addition to polymer stabilization. For example, it may be desirable to react the phosphite composition to form a new derivative product, that may have additional uses. Transesterification processes, for example, such as those disclosed in Hechenbleikner et al., U.S. Pat. No. 3,056,823, which is incorporated herein by reference, may also be employed. Specifically, the process described by Hechenbleikner et al. involves transesterifying a triaryl phosphite with a monohydroxy hydrocarbon in the presence of a small but catalytically effective amount of a metal alcoholate or metal phenolate. To avoid contamination, the alcoholate of the particular alcohol to be transesterified is employed. Instead of employing a preformed alcoholate, the alcoholate can be formed in situ by adding the metal, e.g., sodium, potassium or lithium to the alcohol prior to adding the triaryl phosphite. The mono alcohol and triaryl phosphite are reacted in the mol ratio of three moll of the alcohol to one mol of the triaryl phosphite.

Without further elaboration, it is believed that one skilled in the art can, using the description herein, utilize the present invention to its fullest extent. The following examples are included to provide additional guidance to those skilled in the art in practicing the claimed invention. The examples provided are merely representative of the work that contributes to the teaching of the present application. Accordingly, these examples are not intended to limit the invention, as defined in the appended claims, in any manner.

The present invention will be better understood in view of the following non-limiting Examples.

EXAMPLES

Examples 1 & 2

Alkylation with Pure Olefin (Comparative)

For each of Examples 1 & 2, a 1 liter 5-necked jacketed vessel, heated by means of circulated oil via a Julabo heater/cooling circulator bath, was fitted with: (i) an overhead stirrer complete with stirring assembly fitted with a PTFE paddle blade stirring at 100 rpm; (ii) a Liebig condenser; and (iii) a digital thermocouple.

150 grams (1.59 mols) of molten phenol was charged under nitrogen to the vessel and heated to 100° C. When the phenol was at 100° C., 25.2 µL (0.28 mmols) of triflic acid was charged to the vessel. 177 grams (3.15 mols) of 2-methylpropene was introduced below the surface of phenol via a sinter glass frit at a uniform rate over 4 hours. The 2-methylpropene lecture bottle was connected to the glass frit using PVC tubing. Once the 2-methylpropene addition was completed, the reaction was held at an oil temperature of 100° C. for several hours.

Examples 3 & 4

Alkylation with Olefin/Saturate Mixture

The procedure described in Examples 1 & 2 was repeated, but using a mixture of 2-methylpropene and 350 grams (3.15 mols) of butane. The gas line from the butane lecture bottle was spliced (using a T-piece) into the gas line from the 2-methylpropene lecture bottle such that the gases could be mixed prior to their introduction to the reaction vessel. A reduction in the amount of late eluting by-products (species with a retention times >20.5 mins) that were seen by GC, as shown in Table 6, compared to alkylation with purified olefins.

TABLE 6

| Example | GC Area % | | | | | | |
|---|---|---|---|---|---|---|---|
| | 20.57 min | 20.91 min | 21.54 min | 24.2 min | 24.3 min | 25.52 min | Sum |
| 1 | 0.15 | 0.57 | 0.27 | 0.15 | 0.17 | 0.55 | 1.86 |
| 2 | 0.39 | 0.56 | 0.27 | 0 | 0 | 0 | 1.22 |
| 3 | 0.17 | 0.25 | 0.09 | 0 | 0 | 0 | 0.51 |
| 4 | 0.21 | 0.26 | 0.09 | 0 | 0 | 0 | 0.56 |

No detrimental affects on the rate of conversion or selectivity were observed when comparing 2-methylpropene diluted with butane with Examples 1 & 2. In addition, 2-methylpropene diluted with butane had the positive affect of reducing (by >50 mol %) the amount of 'heavy' by-products, thus reducing the amount of waste. This was demonstrated by a reduction in the amount of late eluting by-products (species with a retention times >20.5 mins) that are seen by GC, as shown in Table 6.

Without being bound by theory, it is believed that by diluting the 2-methylpropene with butane, the rate of dimerization was reduced and hence the amount of diisobutylene generated was also reduced. This led to a reduction on the amount of unwanted 'heavy' by-products. Presumably, the same benefits would arise if 2-methylpropene were diluted with any inert substance that was a gas at the reaction temperature, e.g., propane, pentane, etc.

In view of the many changes and modifications that can be made without departing from principles underlying the invention, reference should be made to the appended claims for an understanding of the scope of the protection to be afforded the invention.

What is claimed is:

1. A process for forming a phosphite composition, comprising
   reacting a hydroxyaryl compound with an olefin in a complex hydrocarbon stream, wherein the complex hydrocarbon stream further comprises saturates to form an alkylate composition comprising two or more alkylated hydroxyaryl compounds; and
   reacting the two or more alkylated hydroxyaryl compounds with a phosphorous trihalide to form the phosphite composition, wherein the phosphite composition comprises:
   tris(monoalkylaryl)phosphite in an amount from 20 to 70 wt %;
   bis(monoalkylaryl)dialkylaryl phosphite in an amount from 15 to 60 wt %,
   tris(dialkylaryl)phosphite in an amount of from 0.1 to 20 wt %; and
   bis(dialkylaryl)monoaryl phosphite in an amount of from 2 to 20 wt %, and is a liquid at ambient conditions.

2. The process of claim 1, wherein the olefin is a branched olefin.

3. The process of claim 2, wherein there is from 45 to 95 wt. % of the branched olefin in the complex hydrocarbon stream.

4. The process of claim 1, wherein there is from 0.5 to 20 wt. % of the saturates in the complex hydrocarbon stream.

5. The process of claim 1, wherein the complex hydrocarbon stream is derived from a fraction of a cracked hydrocarbon feed stream.

6. The process of claim 1, wherein the complex hydrocarbon stream is derived from reaction products of a dehydrogenation of a paraffinic feedstock.

7. The process of claim 1, wherein the complex hydrocarbon stream contains at least 80 wt. % of hydrocarbons having a same number of carbon atoms.

8. The process of claim 7, wherein the number of carbon atoms is from 2 to 18 carbons.

9. The process of claim 1, wherein the hydroxyaryl compound is selected from the group consisting of phenol, 1-naphthol 2-naphthol, 9-phenanthrol, indanol, catechol, resorcinol, anthracen-2-ol, 4-biphenol, 4,4'-biphenol, xylenol, cresol, and derivatives thereof.

10. The process of claim 1, further separating unreacted components of the complex hydrocarbon stream from the reaction mixture.

11. A process for forming a phosphite composition comprising
    tris(monoalkylaryl)phosphite in an amount from 20 to 70 wt %;
    bis(monoalkylaryl)dialkylaryl phosphite in an amount from 15 to 60 wt %,
    tris(dialkylaryl)phosphite in an amount of from 0.1 to 20 wt %; and
    bis(dialkylaryl)monoaryl phosphite in an amount of from 2 to 20 wt %, the process comprising the steps of:
    (a) providing a complex hydrocarbon stream comprising at least one olefin and at least one saturate compound;
    (b) contacting a hydroxyaryl with the complex hydrocarbon stream under conditions effective to form two or more alkylated hydroxyaryls in a reaction mixture;
    (c) separating the at least one saturate compound from the reaction mixture; and
    (d) reacting the two or more alkylated hydroxyaryls with a phosphorous trihalide to form the phosphite composition, wherein the phosphite composition is liquid at ambient conditions.

* * * * *